US011433196B2

(12) United States Patent
Liu et al.

(10) Patent No.: US 11,433,196 B2
(45) Date of Patent: Sep. 6, 2022

(54) WATER OUT ALARM DETERMINATION

(71) Applicant: Fisher & Paykel Healthcare Limited, Auckland (NZ)

(72) Inventors: Po-Yen Liu, Auckland (NZ); Ivan Chih-Fan Teng, Auckland (NZ); Stefan Leo Van Workum, Auckland (NZ); Oliver Samuel Steiner, Auckland (NZ); Anthony James Newland, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 226 days.

(21) Appl. No.: 16/319,798

(22) PCT Filed: Jul. 19, 2017

(86) PCT No.: PCT/NZ2017/050096
§ 371 (c)(1),
(2) Date: Jan. 22, 2019

(87) PCT Pub. No.: WO2018/016974
PCT Pub. Date: Jan. 25, 2018

(65) Prior Publication Data
US 2019/0262560 A1 Aug. 29, 2019

Related U.S. Application Data

(60) Provisional application No. 62/364,250, filed on Jul. 19, 2016.

(51) Int. Cl.
*A61M 16/00* (2006.01)
*A61M 16/10* (2006.01)
(Continued)

(52) U.S. Cl.
CPC .... *A61M 16/0051* (2013.01); *A61M 16/0069* (2014.02); *A61M 16/024* (2017.08);
(Continued)

(58) Field of Classification Search
CPC .............. A61M 16/00; A61M 16/0003; A61M 16/0051; A61M 16/0066; A61M 16/0069;
(Continued)

(56) References Cited

U.S. PATENT DOCUMENTS 6,078,729 A 6/2000 Kopel
6,802,314 B2 10/2004 McPhee
(Continued)

FOREIGN PATENT DOCUMENTS

EP 0885623 61 12/1998
WO WO 2011/078706 A2 6/2011
(Continued)

OTHER PUBLICATIONS

International Search Report and Written Opinion of the International Searching Authority issued in International Application No. PCT/NZ2017/050096, dated Oct. 17, 2017, in 22 pages.

*Primary Examiner* — Joseph D. Boecker
(74) *Attorney, Agent, or Firm* — Knobbe, Martens, Olson & Bear, LLP

(57) ABSTRACT

The present disclosure provides for an improved method of determining a water out condition in a humidified gases supply apparatus. The method includes a two-step process including a primary determination of a water out condition and a secondary determination of a water out condition. This primary determination is made during observation of the normal operation of the apparatus. During the secondary determination the method takes temporary control over the humidifying part of the apparatus. The secondary determination confirms or contradicts the primary determination.

18 Claims, 9 Drawing Sheets

(51) Int. Cl.
*A61M 16/06* (2006.01)
*A61M 16/16* (2006.01)
*G08B 21/18* (2006.01)
*G08B 5/36* (2006.01)
*G08B 23/00* (2006.01)
*G08B 3/10* (2006.01)

(52) U.S. Cl.
CPC ...... *A61M 16/0666* (2013.01); *A61M 16/109* (2014.02); *A61M 16/1095* (2014.02); *A61M 16/16* (2013.01); *G08B 3/10* (2013.01); *G08B 5/36* (2013.01); *G08B 21/182* (2013.01); *G08B 23/00* (2013.01); *A61M 2016/0033* (2013.01); *A61M 2016/0039* (2013.01); *A61M 2205/3368* (2013.01); *A61M 2205/3386* (2013.01); *A61M 2205/3389* (2013.01)

(58) Field of Classification Search
CPC .............. A61M 16/022; A61M 16/024; A61M 16/0666; A61M 16/109; A61M 16/1095; A61M 16/16; A61M 2016/0033; G08B 23/00; G08B 21/182
See application file for complete search history.

(56) References Cited

U.S. PATENT DOCUMENTS

| | | | |
|---|---|---|---|
| 8,739,780 B2 | 6/2014 | Tang et al. | |
| 8,873,941 B2 | 10/2014 | Row et al. | |
| 9,393,379 B2 | 7/2016 | Barker et al. | |
| 9,440,042 B2 | 9/2016 | McAuley et al. | |
| 2002/0129815 A1* | 9/2002 | McPhee | A61M 16/109 128/200.24 |
| 2005/0223244 A1* | 10/2005 | Sinai | G06F 1/3296 713/300 |
| 2013/0104886 A1* | 5/2013 | Barker | A61M 16/1075 128/203.14 |
| 2013/0131580 A1* | 5/2013 | Blackhurst | A61B 18/00 604/26 |
| 2013/0174841 A1* | 7/2013 | McAuley | A61M 16/0666 128/203.14 |
| 2013/0298908 A1 | 11/2013 | Tang et al. | |
| 2014/0352694 A1 | 12/2014 | Row et al. | |
| 2015/0014874 A1 | 1/2015 | Winski | |
| 2015/0096560 A1* | 4/2015 | Klenner | A61M 16/0816 128/202.27 |
| 2016/0256659 A1* | 9/2016 | Poormand | A61M 16/109 |
| 2017/0028159 A1* | 2/2017 | Ghalib | A61M 16/16 |

FOREIGN PATENT DOCUMENTS

| | | |
|---|---|---|
| WO | WO 2011/136664 A1 | 11/2011 |
| WO | WO 2014/052983 A1 | 4/2014 |
| WO | WO 2014/102660 A1 | 7/2014 |
| WO | WO 2015/058255 A1 | 4/2015 |
| WO | WO 2015/160268 A1 | 10/2015 |
| WO | WO-2015160268 A1 * | 10/2015 ............. A61B 17/34 |

* cited by examiner

WATER OUT ALARM DETERMINATION

INCORPORATION BY REFERENCE TO PRIORITY APPLICATION

This application claims priority from U.S. provisional application 62/364,250, filed 19 Jul. 2016. The entire contents of US62/364,250 are hereby incorporated by reference.

FIELD OF THE DISCLOSURE

The present disclosure relates to humidification systems for gases to be supplied to a patient.

BACKGROUND

For a range of applications, it is beneficial to humidify gases being supplied to a patient. These applications include where the gases are for breathing by the patient and where the gas is being supplied during surgery to the patient. In the case of breathing gases, the humidity increases patient comfort and the humidified gases are less prone to drying out the tissues of the patient airway. In the case of surgical gases, the humidified gases reduce the drying out of exposed tissue and improve post-operative outcomes.

SUMMARY

In a gases humidification system incorporating a humidification chamber for humidifying gases for supply to the patient, it is important that a certain minimum level of water is maintained in order for the humidifier to have the ability to supply water vapor to the gases flow. Accordingly, it is important for a healthcare professional administering the humidified gases to a patient, or the patient themselves in the case of home-based administration, to check the water level and add more water when required. This task is often overlooked resulting in a break in operation of the humidification of the airflow or, in some cases, damage to the respiratory assistance device.

Although water out alarms have been incorporated into respiratory humidification devices, the alarms are often susceptible to false alarms in situations where the chamber is not actually empty. False alarms often cause significant concern to non-healthcare professionals who are unsure if the device is working properly. False alarms, when they occur often, also cause healthcare professionals to ignore true alarms when they do occur.

The present disclosure provides a system for optimizing alarm criteria selection to minimize the risk of a false alarm. The present disclosure provides multiple different methods for determining a water out condition and a selection criteria based on operating conditions for selecting an advantageous water out determination method.

It is an object of the present disclosure to provide a breathing assistance apparatus which goes some way to overcoming the abovementioned disadvantages or which at least provides the public or healthcare professionals with a useful choice.

Accordingly in a first aspect, the disclosure may broadly be said to comprise a respiratory assistance system for humidifying a flow of gases comprising: a humidification chamber comprising an inlet and an outlet to allow gases to pass through the humidification chamber, the humidification chamber adapted to hold a quantity of water, a heater adjacent the humidification chamber, the heater adapted to provide heat to the quantity of water in the humidification chamber, a flow sensor positioned on the humidification chamber, a temperature sensor associated with the humidification chamber, and a controller in electronic communication with heater plate, the flow sensor and the temperature sensor, wherein the controller is configured to determine at least one operational state based on a therapy mode and a flow rate and to select at least one water out detection method based on the determined operational state. The operational state is dependent on the flow rate in relation to a flow rate threshold.

The water out detection methods can include a passive water out detection method, an active water out detection method, and a passive water out detection method in conjunction with an active water out detection method.

The respiratory assistance system can also include a user interface configured to permit a person to select the therapy mode from a predetermined list of therapy modes. The predetermined list incorporates an invasive mode, a non-invasive mode, and a high flow, unsealed therapy mode.

To those skilled in the art to which the disclosure relates, many changes in construction and widely differing embodiments and applications of the disclosure will suggest themselves without departing from the scope of the disclosure as defined in the appended claims. The disclosures and the descriptions herein are purely illustrative and are not intended to be in any sense limiting.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

BRIEF DESCRIPTION OF THE DRAWINGS

Preferred embodiments of the present disclosure will be described with reference to the accompanying drawings.

DETAILED DESCRIPTION

The present description provides a respiratory assistance system configured to supply multiple therapy modes and determine whether the water level within a humidification chamber has reached below an acceptable threshold level. The system selects an appropriate water out detection method based on the operational state of the system, which in turn relates to the particular therapy mode selected by a user and a gases flow rate. The system therapy modes can include an invasive, non-invasive, and a high flow, unsealed mode or any other modes known to those of skill in the art. The high flow, unsealed therapy mode (herein referred to as Optiflow® mode) is marketed as Optiflow® by Fisher and Paykel Healthcare Limited of Auckland, New Zealand.

Figure 4A:
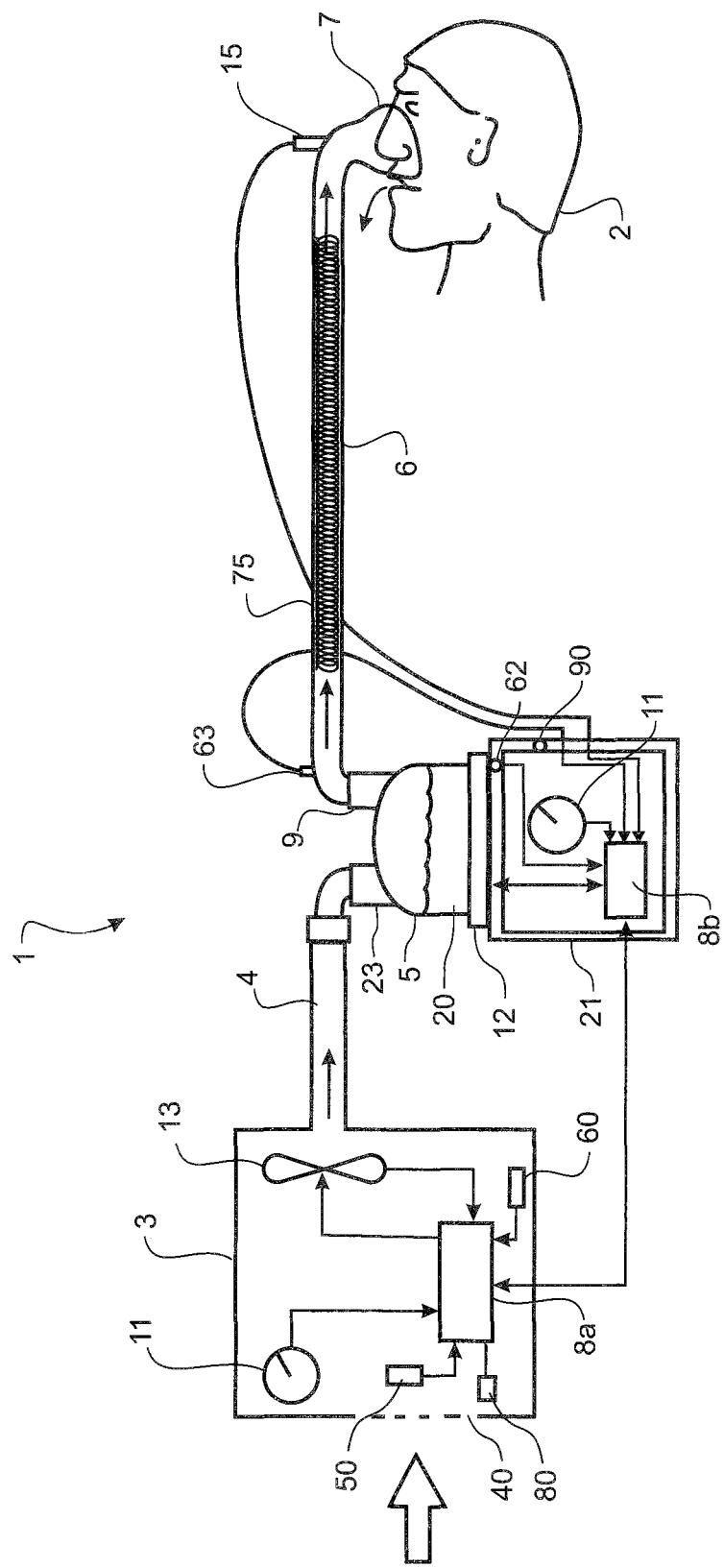
FIG. 4a shows a schematic view of a user receiving humidified air, with the user wearing a nasal mask and receiving air from a modular blower/humidifier breathing assistance system.
Figure 4B:
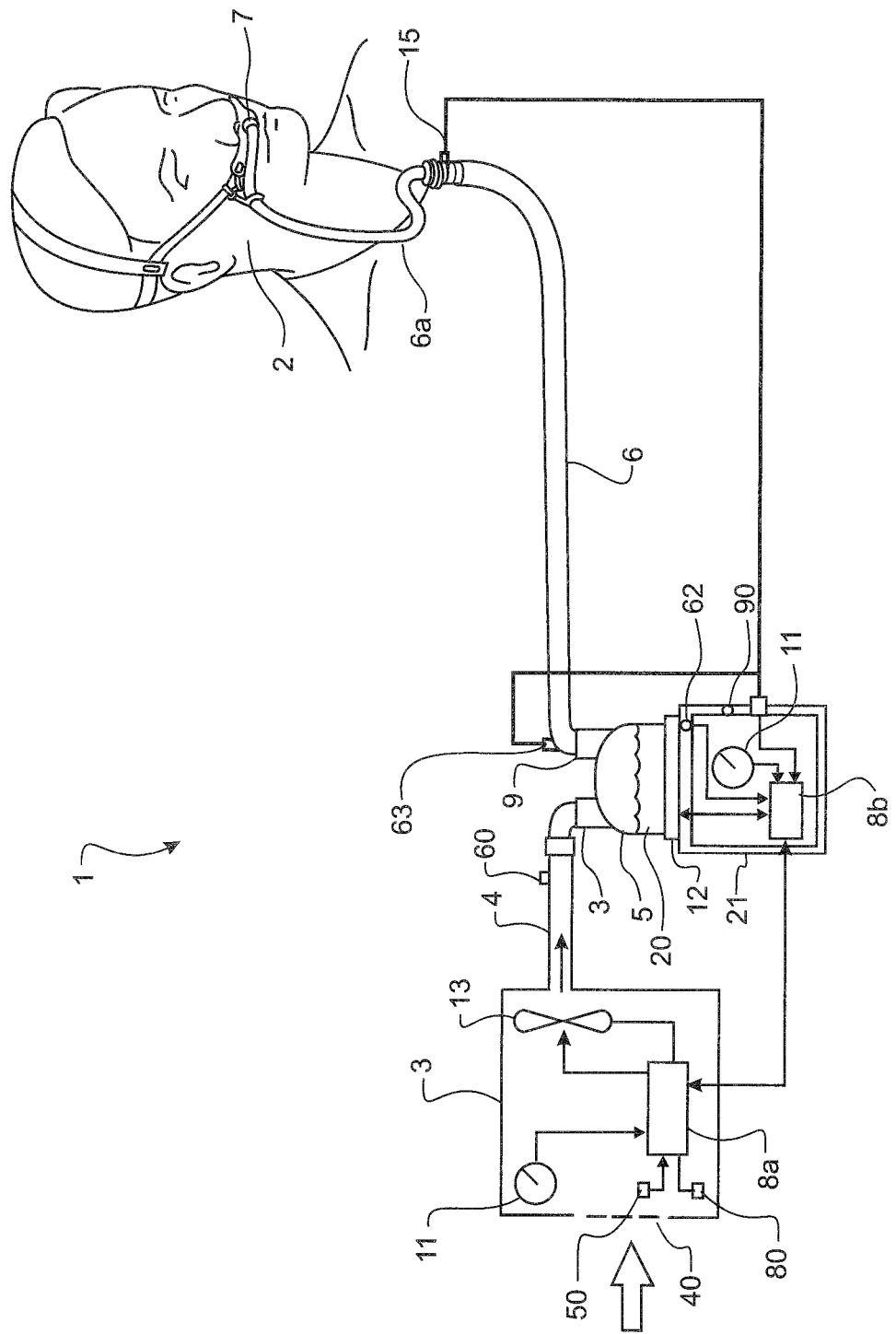
FIG. 4b shows a schematic view of a user receiving humidified air, where the user is wearing a nasal cannula and receiving air from a modular blower/humidifier breathing assistance system.

A schematic view of a user 2 receiving air from a respiratory assistance breathing unit and humidifier system 1 according to a first example system configuration is shown in FIGS. 4a and 4b. The system 1 provides a pressurized stream of heated, humidified gases to the user 2 for therapeutic purposes, including, for example, to reduce the incidence of obstructive sleep apnea, to provide CPAP therapy, to provide humidification for therapeutic purposes, or similar. The system 1 is described in detail below.

The assisted breathing unit or blower unit 3 has an internal compressor unit, flow generator or fan unit 13—generally this could be referred to as a flow control mechanism. Air from atmosphere enters the housing of the blower unit 3 via an atmospheric inlet 40, and is drawn through the fan unit 13. The output of the fan unit 13 is adjustable—the fan speed is variable. The pressurized gases stream exits the fan unit 13 and the blower unit 3 and travels via a connection conduit 4 to a humidifier chamber 5, entering the humidifier chamber 5 via an entry port or inlet port 23.

In alternative embodiments, the assisted breathing unit may comprise a ventilator. The ventilator may have fans or turbines configured to generate air flow. In some embodiments, the ventilators may receive gases from a compressed air source, such as a tank. The ventilators may then use valves to control the delivery of air to the humidification chamber 5.

The humidifier chamber 5 in use contains a volume of water 20. In some embodiments, in use the humidifier chamber 5 is located on top of a humidifier base unit 21 which has a heater plate 12. The heater plate 12 is powered to heat the base of the chamber 5 and thus heat the contents of the chamber 5. As the water in the chamber 5 is heated it evaporates, and the gases within the humidifier chamber 5 (above the surface of the water 20) become heated and humidified. The gases stream entering the humidifier chamber 5 via inlet port 23 passes over the heated water (or through these heated, humidified gases—applicable for large chamber and flow rates) and becomes heated and humidified as it does so. The gases stream then exits the humidifier chamber 5 via an exit port or outlet port 9 and enters a delivery conduit 6.

When a 'humidifier unit' is referred to in this specification with reference to the disclosure, this should be taken to mean at least the chamber 5, and if appropriate, the base unit 21 and heater plate 12.

The heated, humidified gases pass along the length of the delivery conduit 6 and are provided to the patient or user 2 via a user interface 7. The conduit 6 may be heated via a heater wire (not shown) or similar to help prevent rain-out.

The user interface 7 shown in FIG. 4a is a nasal mask which surrounds and covers the nose of the user 2. However, it should be noted that a nasal cannula (as shown in FIG. 4b), full face mask, tracheostomy fitting, or any other suitable user interface could be substituted for the nasal mask shown. A central controller or control system 8 is located in either the blower casing (controller 8a) or the humidifier base unit (controller 8b). In modular systems of this type, a separate blower controller 8a and humidifier controller 8b may be used, and the controllers 8a, 8b may be connected (e.g. by cables or similar) so they can communicate with one another in use. In some embodiments, the controllers may be independent from one another. The humidifier controller 8b may be an independent unit configured for use with any type of gas source.

In some embodiments, the blower controller 8a and the humidifier controller 8b are in a master-servant relationship—generally this could refer to the capability of one of the controller to control the functions of the other controller. In an alternative embodiment, the blower controller 8a and the humidifier controller 8b are in a peer relationship—generally this could refer to capability of each controller to function independently of the other.

In some embodiments, the control system 8 receives user input signals via user controls 11 located on either the humidifier base unit 21, or on the blower unit 3, or both. In some embodiments the controller 8 also receives input from sensors located at various points throughout the system 1. In alternative embodiments, the humidifier may include a vertical wall or spine having user controls 11 located on the spine. The user controls may be positioned above the humidification chamber 5 and the heater plate 12. This would provide the user with the ability to interact with the user controls with minimal risk of touching the heater plate 12.

The sensors and their locations will be described in more detail below. In response to the user input from controls 11, and the signals received from the sensors, the control system 8 determines a control output which in some embodiments sends signals to adjust the power to the humidifier chamber heater plate 12 and the speed of the fan 13. The programming which determines how the controller determines the control output will be described in more detail below.

Figure 5:
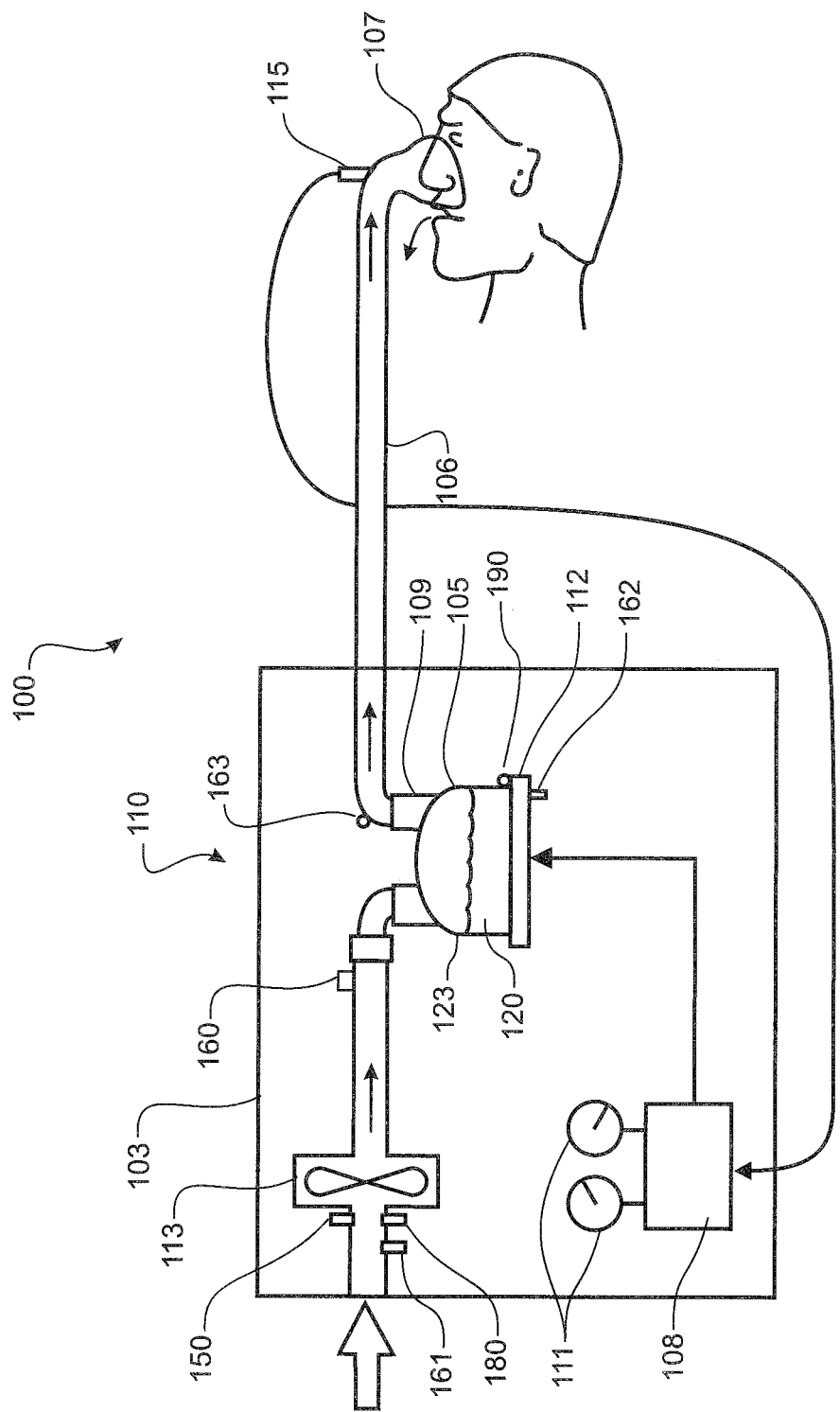
FIG. 5 shows a schematic view of a user receiving humidified air, where the user is wearing a nasal mask and receiving air from an integrated blower/humidifier breathing assistance system.

A schematic view of the user 2 receiving air from an integrated blower/humidifier system 100 according to a second form of the disclosure is shown in FIG. 5. The system operates in a very similar manner to the modular system 1 shown in FIG. 4 and described above, except that the humidifier chamber 105 has been integrated with the blower unit 103 to form an integrated unit 110. A pressurized gases stream is provided by fan unit 113 located inside the casing of the integrated unit 110. The water 120 in the humidifier chamber 105 is heated by heater plate 112 (which is an integral part of the structure of the blower unit 103 in this embodiment). Air enters the humidifier chamber 105 via an entry port 123, and exits the humidifier chamber 105 via exit port 109. The gases stream is provided to the user 2 via a delivery conduit 106 and an interface 107. The controller 108 is contained within the outer shell of the integrated unit 100. In the illustrated embodiment, the controller 108 is a single controller that controls the heater plate 112 and the operation of the blower unit 103 based on one or more sensor inputs. The controller 108 may comprise individual software or hardware modules to control the blower unit 103 and the heater plate 112. User controls 111 are located on the outer surface of the unit 100.

Figure 6:
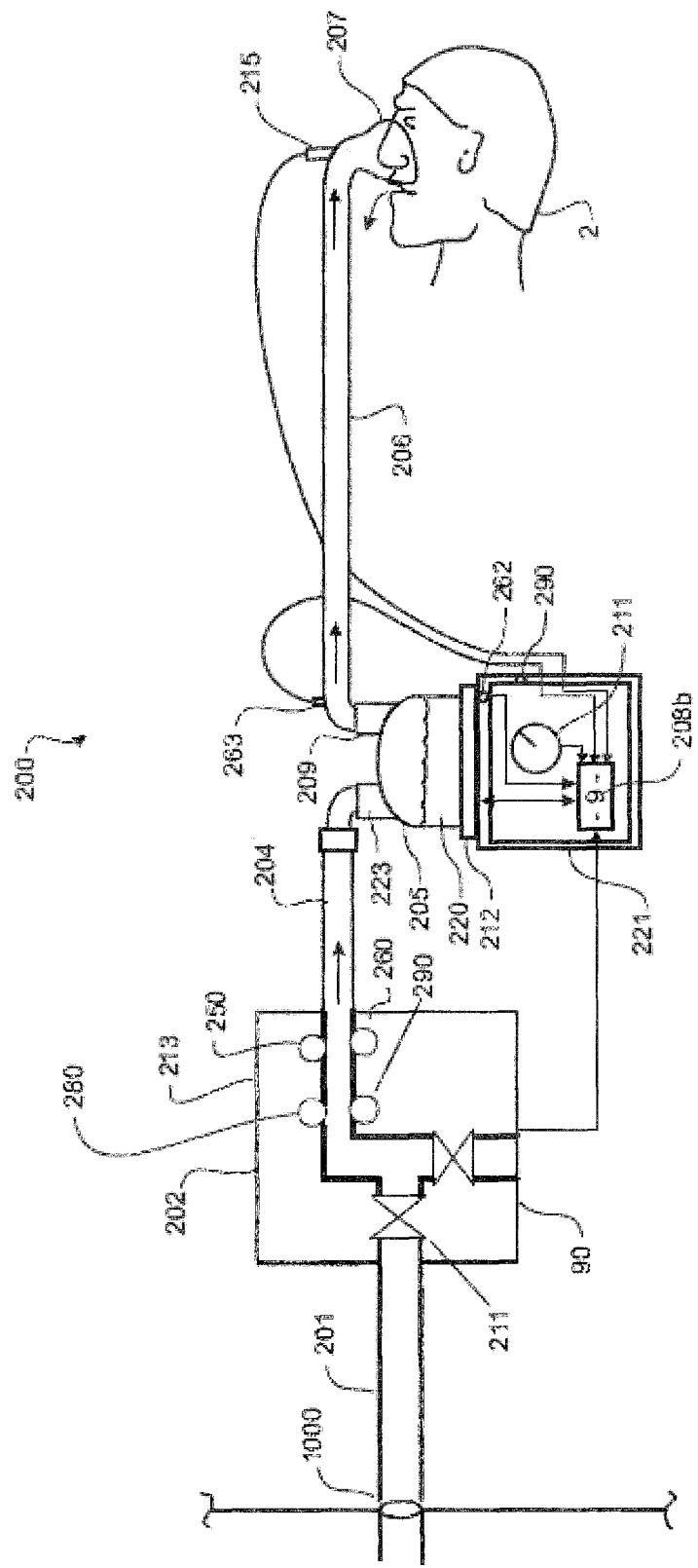
FIG. 6 shows a schematic view of a user receiving humidified air, where the user is wearing a nasal cannula, the breathing assistance system receiving gases from a central source via a wall inlet and providing these to a control unit, which provides the gases to a humidifier chamber in line with and downstream of the control unit.

A schematic view of the user 2 receiving air from a further form of breathing assistance system 200 is shown in FIG. 6. The system 200 can be generally characterized as a remote source system, and receives air from a remote source via a wall inlet 1000.

The wall inlet 1000 is connected via an inlet conduit 201 to a control unit 202, which receives the gases from the inlet 1000. The control unit 202 has sensors 250, 260, 280, 290 which measure the humidity, temperature and pressure and flow respectively of the incoming gases stream.

The gases flow is then provided to a humidifier chamber 205, with the gases stream heated and humidified and provided to a user in a similar manner to that outlined above. It should be noted that when 'humidifier unit' is referred to for a remote source system such as the system 200, this should be taken to mean as incorporating the control unit 202—the gases from the remote source can either be connected directly to an inlet, or via the control unit 202 (in order to reduce pressure or similar), but the control unit and the humidifier chamber should be interpreted as belonging to an overall 'humidifier unit'.

In some embodiments, the system 200 can provide $O_2$ or an $O_2$ fraction to the user. The system may provide $O_2$ to the user by having the central source as an $O_2$ source. In an alternative embodiment, the system may provide $O_2$ by blending atmospheric air with incoming $O_2$ from the central source. The blending of atmospheric air and incoming $O_2$ may occur via a venturi 90 or similar located in the control unit 202.

The control unit 202 may also have a valve 211 or a similar mechanism to act as a flow control mechanism to adjust the flow rate of gases through the system 200. Additionally, the control unit may also have a plurality of valves to control the flow rate of gases through the system 200. In some embodiments, the valve 211 operation may be controlled by the controller 9. In an alternative embodiment, the valve 211 operation may be controlled by an additional controller located within the control unit 202.

Sensors

The modular and integrated systems 1, 100 and 200 shown in FIGS. 4, 5 and 6 have sensors located at points throughout the system. These will be described below in relation to the breathing assistance system 1.

In an embodiment, the modular system 1, as shown in FIG. 4, has at least the following sensors in the following locations:

1) An ambient temperature sensor 60 located within, near, or on the blower casing, configured or adapted to measure the temperature of the incoming air from atmosphere. Temperature sensor 60 may be located in the gases stream after (downstream of) the fan unit 13, and as close to the inlet or entry to the humidifier chamber as possible.

2) A humidifier unit exit port temperature sensor 63 located either at the chamber exit port 9, or located at the apparatus end (opposite to the patient end) of the delivery conduit 6. Outlet temperature sensor 63 is configured or adapted to measure the temperature of the gases stream as it exits chamber 5 (in either configuration the exit port temperature sensor 63 can be considered to be proximal to the chamber exit port 9).

Similarly, sensors are arranged in substantially the same locations in the integrated system 100 shown in FIG. 5 and the system 200 of FIG. 6. For example, for the integrated system of FIG. 5, an ambient temperature sensor 160 is located within the blower casing in the gases stream, just before (upstream of) the humidifier chamber entry port 123. A chamber exit port temperature sensor 163 is located either at the chamber exit port 109 and is configured to measure the temperature of the gases stream as it exits chamber 105 (in either configuration the exit port temperature sensor 163 can be considered to be proximal to the chamber exit port 109). Alternatively, this sensor can be located at the apparatus end (opposite to the patient end) of the delivery conduit 106, for either embodiment. A similar numbering system is used for the breathing assistance system shown in FIG. 6—ambient temperature sensor 260, fan unit 213, chamber exit port temperature sensor 263 located at the chamber exit port 209, etc.

In an embodiment, the breathing assistance system 1 (and 100, 200) has a heater plate temperature sensor 62 located adjacent to the heater plate 12, configured to measure the temperature of the heater plate. The breathing assistance system(s) having a heater plate temperature sensor may be used as it gives an immediate indication of the state of the heater plate. This sensor should be in the heat path between the source of the heat and the reservoir. So, for example, a sensor on a conductive plate that contacts the water chamber on one side and has a heater on the other side may be used.

In an embodiment, the systems have a flow sensor located upstream of the fan unit 13 and configured to measure the gases flow. The location for the flow sensor can be upstream of the fan unit, although the flow sensor can be located downstream of the fan, or anywhere else appropriate. In some embodiments, the flow sensor may be located at the outlet 9 adjacent to a temperature sensor 63. The flow sensor can form part of the system, but it is not absolutely necessary for a flow sensor to be part of the system.

In an embodiment, the system may include a temperature sensor 63 located at the outlet 9 to the humidification chamber 5. In an alternative embodiment, the temperature sensor 63 may be located at the inlet 23 to the humidification chamber 5. The temperature sensor 63 may be configured to also function as a flow sensor based on the polarity of voltage applied to the temperature sensor 63 or the level of voltage applied to the temperature sensor 63.

The layout and operation of the breathing assistance system 1 will now be described below in detail. The operation and layout of the systems 100 and 200 is substantially the same, and will not be described in detail except where necessary.

For the breathing assistance system 1, the readings from all of the sensors are fed back to the control system 8. The control system 8 also receives input from the user controls 11.

Further Alternative Sensor Layouts

In a variant of the apparatus and method outlined above, the system (system 1 or system 100 or system 200) also has additional sensors as outlined below.

3) A patient end temperature sensor 15 (or 115 or 215) is located at the patient end of the delivery conduit 6 (or alternatively in or on the interface 7). That is, at or close to the patient or point of delivery. When read in this specification, 'patient end' or 'user end' should be taken to mean either close to the user end of the delivery conduit (e.g. delivery conduit 6), or in or on the patient interface 7. This applies unless a specific location is otherwise stated. In either configuration, patient end temperature sensor 15 can be considered to be at or close to the user or patient 2.

Operational State Determination

Figure 1A:
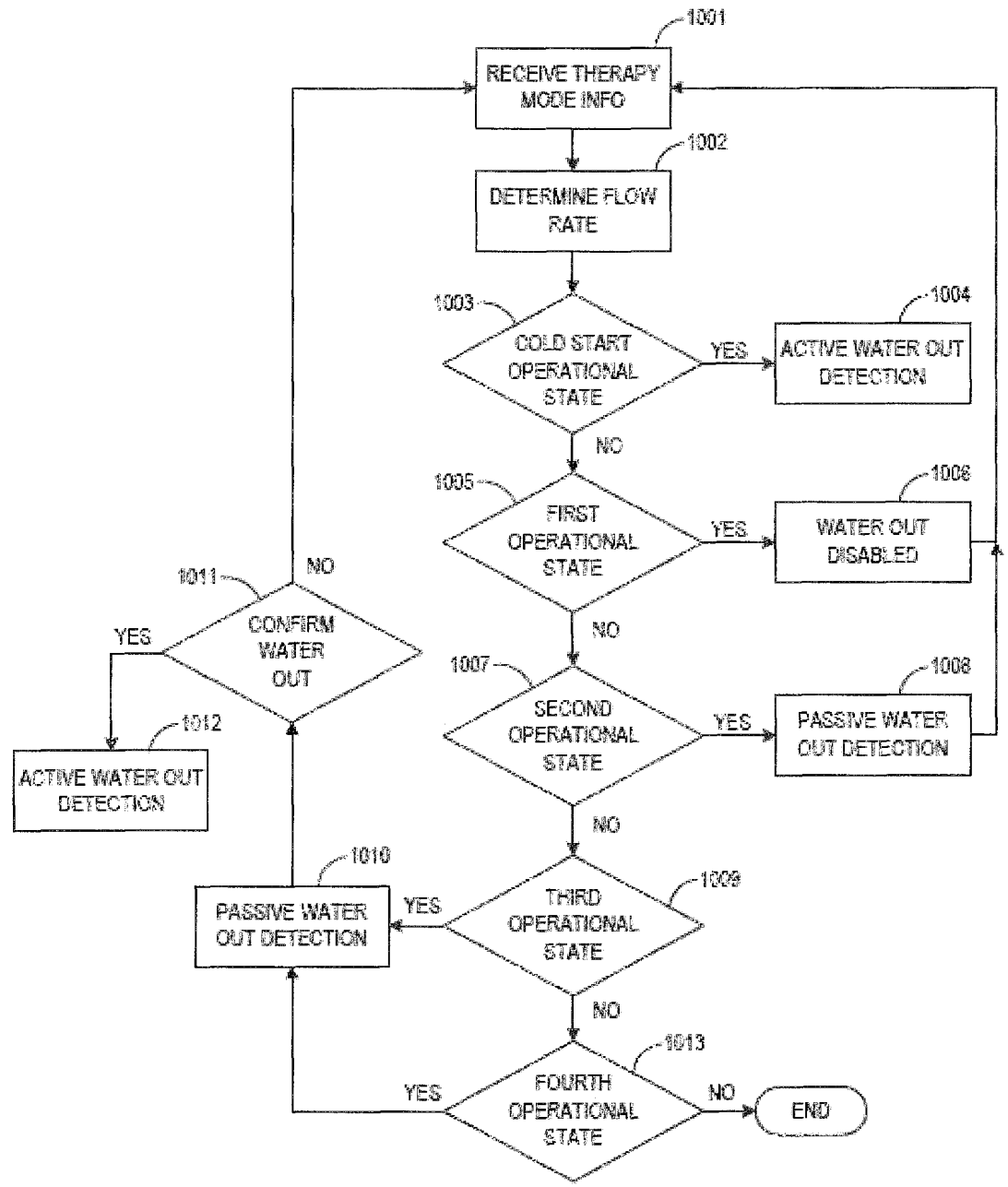
FIG. 1a is a flow diagram illustrating the overall process for determining an absence of water in a humidifier chamber in accordance with the present disclosure.
Figure 1B:
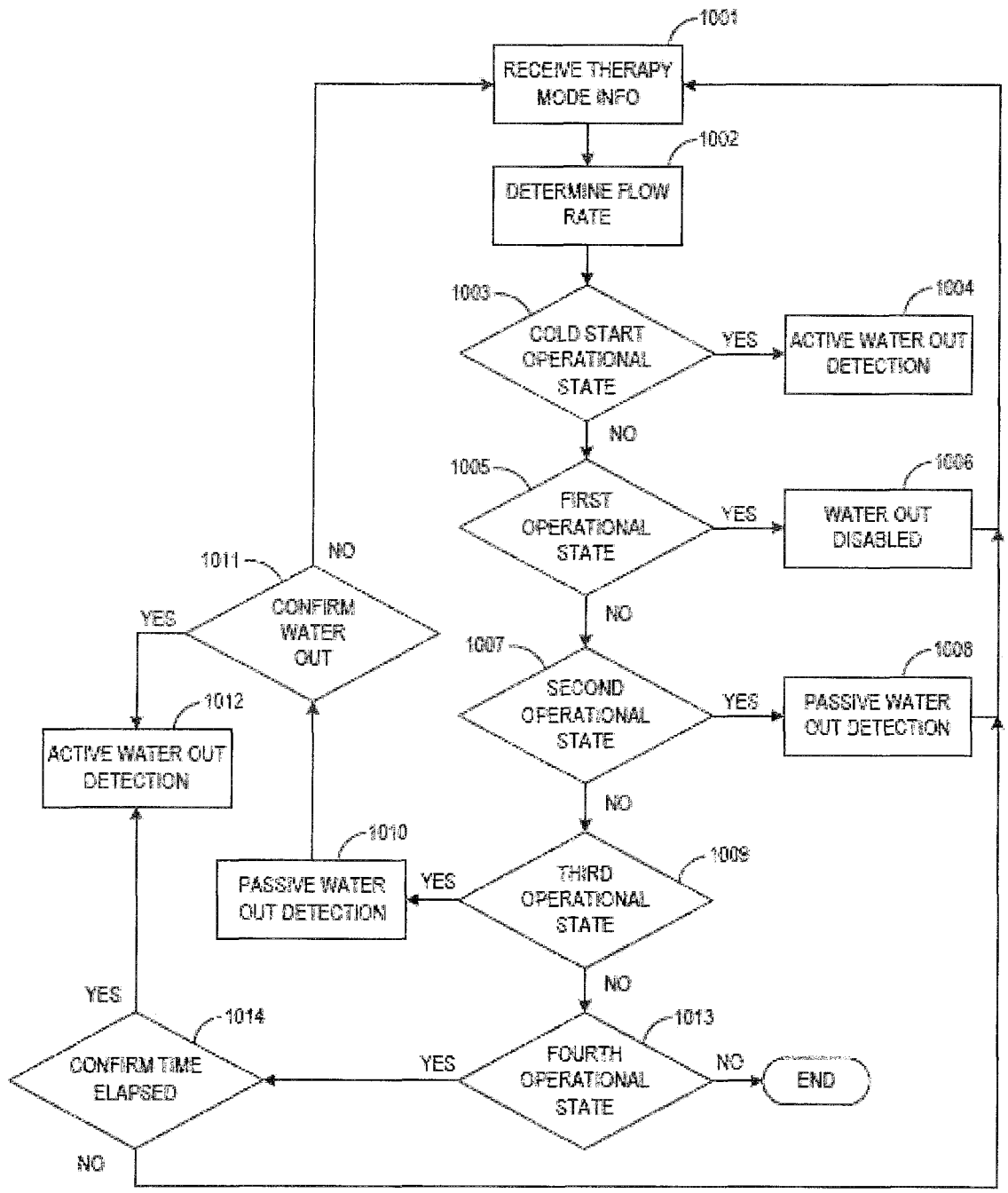
FIG. 1b is a flow diagram illustrating another embodiment of the overall process for determining an absence of water in a humidifier chamber in accordance with the present disclosure.

According to some embodiments, the respiratory assistance system incorporates a routine configured to select the appropriate water out detection method to determine whether the humidification chamber 5 requires the addition of water based on the operational state of the system. The operational state relates to a user selected therapy mode for the system and a gases flow rate. This routine, as discussed in further detail below and may be run at any suitable time interval. In some embodiment, the routine is executed every 10 minutes. This allows the heater plate to adequately cool in the event that an active test has been previously executed. However, in alternative embodiments, the routine could be executed every few seconds or every few milliseconds. The routine is illustrated in FIGS. 1*a* and 1*b*. FIGS. 1*a* and 1*b* illustrate alternative embodiments for control of the system at the fourth operational state.

While the decision steps are described in a sequential manner, the system may perform the steps in a different sequence or concurrently, as well. As illustrated in step 1001, a controller 8 receives information relating to the system's therapy mode. The controller 8 then proceeds to determine the system's flow rate at step 1002. The flow rate may be determined through a flow sensor positioned on the humidification chamber 5, specifically at either the inlet 23 or outlet ports 9. Alternatively, the flow sensor may be positioned downstream to the fan unit 13 associated with the blower unit 3. The controller 8 utilizes the received therapy mode and flow rate information to determine the system's operational state. Based on the system's operational mode and flow rate, the controller 8 selects the appropriate water out detection method.

Cold Start Operational State

At step 1003, the controller 8 determines whether the system is in a cold start operational state. After startup, the system is determined to be in a cold start operational state until: (i) the heater plate temperature exceeds a defined temperature threshold, (ii) a defined time threshold since startup of the system is satisfied, (iii) the temperature at the chamber outlet exceeds a defined temperature threshold, and/or (iv) the temperature at the patient end exceeds a defined temperature threshold. The heater plate temperature, chamber outlet temperature and patient end temperature can be determined by their respective temperature sensors, such as for example temperature sensors 62, 63, and 15. The defined temperature thresholds of the heater plate, the chamber outlet, and patient end can be temperatures greater than 30 degrees Celsius, such as, for example 35 degrees Celsius, 37 degrees Celsius, 40 degrees Celsius, 42 degrees Celsius, and/or another defined temperature that is a sufficient temperature for respective component after startup of the system. Each defined temperature threshold of the heater plate, the chamber outlet, and patient end can be separately defined. For example, in a preferred embodiment, the heater plate temperature threshold is 40 degrees Celsius, the chamber outlet temperature threshold is 37 degrees Celsius, and the patient end temperature threshold is 40 degrees Celsius. In some embodiments, the system chamber outlet includes a defined flow rate threshold and a temperature threshold. The flow rate threshold can be any non-zero flow rate, such as, for example about or greater than 0.5 L/min, about or greater than 3 L/min, or another non-zero flow rate. For example, the chamber outlet temperature threshold can be 37 degrees Celsius with a flow rate threshold of 3 L/min. The defined time threshold for the time measured since startup of the system can be 2 minutes, 5 minutes, 10 minutes, 20 minutes, and/or any other defined time period that provides sufficient time for the heater plate to heat up after startup of the system. The cold start operational state is not dependent on therapy mode or flow rate. In some alternative embodiments, the cold start operational state can be dependent at least in part on the flow rate.

If the controller 8 determines the system satisfies the criteria to be in the cold start operational state, the controller 8 proceeds to an active water out detection method at step 1004. If the active water out detection method returns a water out condition, the alarm is activated with a setup error and/or a water out alarm. If the controller 8 determines the system does not satisfy the criteria to be in cold start operational state, the controller 8 proceeds to the step 1005. In some embodiments, the default operational state after startup of the system is the cold start operational state. The system will stay in the cold start operational state until one of the criteria for exiting the cold start operational mode has been satisfied. For example, the system will stay in the cold start operational mode until the time threshold is satisfied or one of the temperatures of the heater plate, the chamber outlet, or the patient inlet exceed their respective temperature thresholds.

First Operational State

At step 1005, the controller 8 determines whether the system is in a first operational state. The system is determined to be in a first operational state (or "no flow" state) when the flow rate is between 0-3 L/min for any selected therapy mode. If the controller 8 determines the system satisfies the criteria to be in a first operational state, the water out alarm is disabled at step 1006. At this low flow rate, false alarms can be common because the water level will not decrease rapidly during a low flow state. The alarm can be disabled without serious concern. When the alarm is disabled, the controller 8 may return back to step 1001. However, if the controller 8 determines the system does not satisfy the criteria to be in a first operational state, the controller 8 proceeds to step 1007.

Second Operational State

At step 1007, the controller 8 determines whether the system is in a second operational state. The system is determined to be in a second operational state when the system is in either an invasive therapy mode or an Optiflow® therapy mode and the flow rate is determined to be at a medium or high flow rate. The flow rate level is based on thresholds that are provided to the system.

When the controller 8 determines that the system satisfies the criteria to be in a second operational state, the controller 8 proceeds to a passive water out detection method at step 1008. If the passive water out detection method returns a water out condition, the alarm is activated without running an active water out detection method. However, if the controller 8 determines the system does not satisfy the criteria to be in a second operational state, the controller 8 proceeds to the following step.

Third Operational State

At step 1009, the controller 8 determines whether the system is in a third operational state. The system is determined to be in a third operational state when the system is in either an invasive therapy mode or an Optiflow® therapy mode and the flow rate is determined to be at a medium or low flow rate.

When the controller 8 determines that the system satisfies the criteria to be in a third operational state, the controller 8 proceeds to a passive water out detection method at step 1010. The passive water out detection method determines whether there is a water out condition at step 1011. If the passive water out detection method returns a water out condition, then the controller proceeds to an active water out detection method at step 1012. As described in further detail below, an active water out detection method is run in conjunction with the passive water out detection method to decrease the likelihood of a false positive alarm for therapy modes with lower set points. If the active water out detection method returns a water out condition, the alarm is activated. However, if the active water out detection method does not return a water out condition, the controller 8 terminates the sequence and reinitiates the routine at the suitable time interval.

Additionally, if the controller 8 determines the system does not satisfy the criteria to be in a third operational state, the controller 8 proceeds to the following step.

Fourth Operational State

At step 1013, the controller 8 determines whether the system is in a fourth operational state. The system is determined to be in a fourth operational state when the system is in a non-invasive therapy mode.

When the controller 8 determines that the system satisfies the criteria to be in a fourth operational state, the controller 8 proceeds to a passive water out detection method at step 1010. If the passive water out detection method returns a water out condition, then the controller 8 proceeds to an active water out detection method at step 1012. If the active water out detection method returns a water out condition, the alarm is activated.

However, if the active water out detection method does not returns a water out condition or the controller 8 determines the system does not satisfy the criteria to be in a fourth operational state, the controller 8 terminates the sequence and reinitiates the routine at the suitable time interval.

With reference now to FIG. 1b, an alternative embodiment for the fourth operational state is illustrated. In FIG. 1b, when the controller 8 determines that the system satisfies the criteria to be in a fourth operational state, the controller 8 proceeds to a time-based active water out detection method at step 1014. At step 1014, the controller 8 determines whether a defined time period has elapsed since the previous active water out detection method was activated or since the system entered the non-invasive therapy mode. If the controller 8 determines that the defined time period has elapsed, then the controller 8 proceeds to an active water out detection method at step 1012. The defined time period can be any defined time interval, such as, for example 15 minutes, 20 minutes 30 minutes, one hour, and the like. If the time period has not elapsed, the controller 8 may return back to step 1001. In some embodiments, the controller 8 will continue to execute the active water detection method at each defined time interval.

Step 1001 can represent ongoing receipt of the information relating to the system's therapy mode according to the system conditions. This ongoing process aims to ensure that the humidification chamber 5 contains sufficient water to keep the delivered gases temperature and humidity at or close to the preferred level. As an ongoing process, the routine monitors for a possible water out condition. However, it should be noted that the routine need not continuously monitor for a possible water out condition. The routine may be run at suitable intervals depending on the system requirements.

Alternative Routine Embodiment

As described in further detail below, in some embodiments, the passive water out detection method may be continuously running since this detection method comprises a calculation based on sensor data collected during the normal course of operation. As such, the method does not impact humidifier operation.

Figure 2:
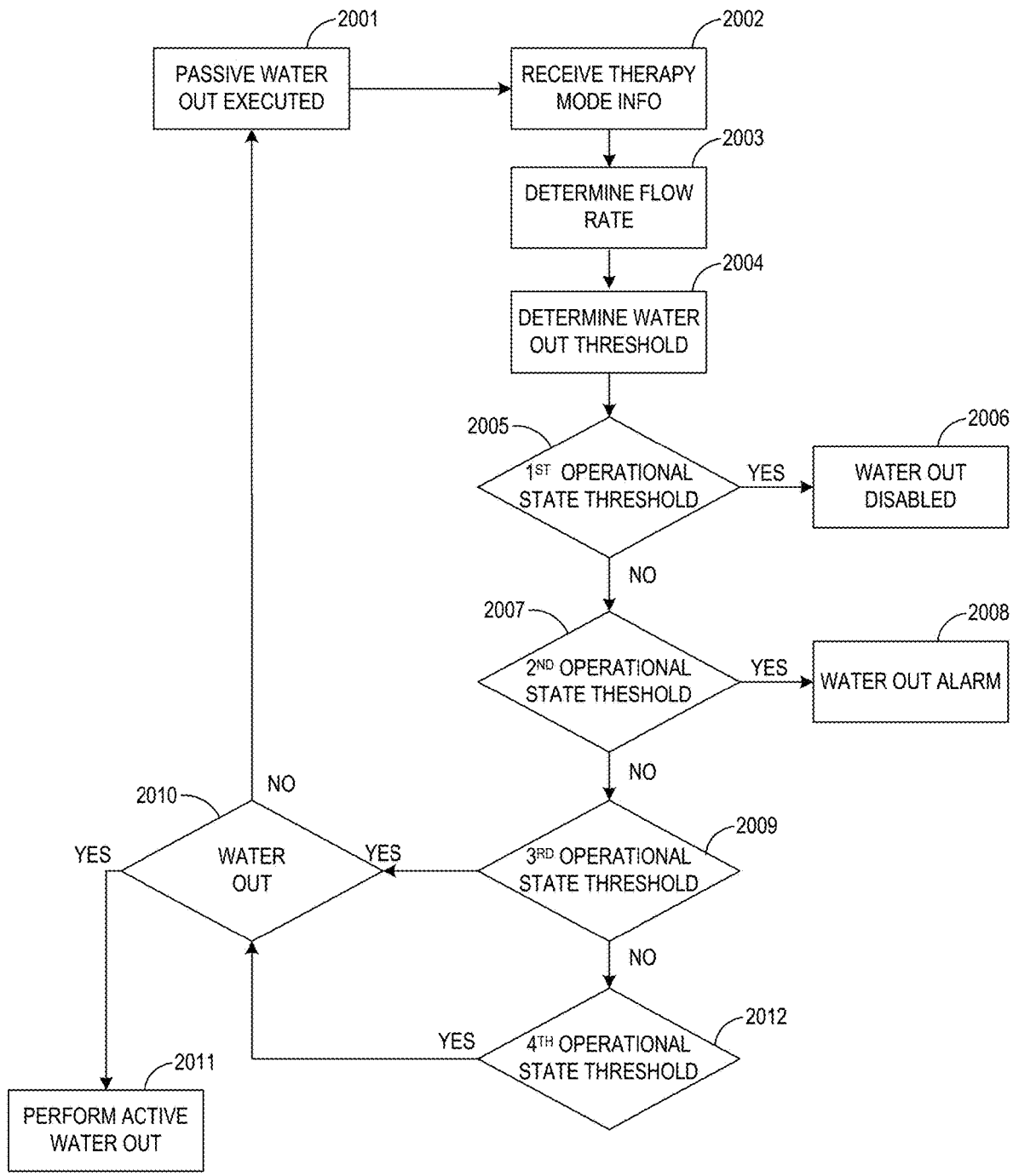
FIG. 2 is a flow diagram illustrating the overall process for determining an absence of water in a humidifier chamber in accordance with an alternative embodiment of the present disclosure.

Accordingly, in an alternative embodiment, as illustrated in FIG. 2, the initiation of the routine, at step 2002, may be triggered based on a first water out condition detected by a continuously run passive water out detection method, as shown in step 2001. The system may then initiate a routine, including steps 2003, 2004, 2005, 2006, 2007, 2008, 2009, 2010, 2011, and 2012, to select the appropriate method capable of accurately determining to determine whether the humidification chamber 5 is dry based on the operational state of the system, similar to the previous embodiment discussed above.

Water Out Detection Methods

Various water out detection methods are described below which are used to determine if a water out condition is present. Each method is used under certain conditions, and the system's routine selects the most appropriate water out detection method based on system's operational state, as previously described in further detail above. Once an appropriate water out detection method is selected, the system utilizes one of the methods described below to determine the existence or non-existence of a water out condition.

Passive Water Out Detection Method

According to the present disclosure, a passive water out detection method determines if a water out condition is present. With reference to FIG. 2, according to an embodiment, the controller 8 evaluates a function of the heater plate power, the heater plate temperature, and the chamber outlet temperature on a continuing basis during normal use of the apparatus. The passive water out detection method is constantly running since it does not impact the humidifier operation. The passive water out detection method runs a calculation of the estimated water level based on sensor data collected during the normal course of operation.

The controller 8 determines the potential for a water out condition when the result of the function below varies from a base line threshold level. The function is a ratio of the chamber outlet temperature from sensor 63 (or 163 or 263) and the heater plate power, as represented by the heater plate duty cycle.

The passive water out detection method estimates the current water level using at least the heater plate power, heater plate temperature, and chamber outlet temperature. In some embodiments, no coefficients or weighting factors are used. The passive water out detection method estimates water level according to the following formula:

$$\text{Estimated Water Level} = \frac{\text{Heater Plate Power}}{\text{Heater Plate Temperature} - \text{Chamber Outlet Temperature}}$$

As the humidification chamber 5 dries, the amount of power required to maintain the same chamber outlet temperature decreases, which is useful for detecting a water out condition. When the estimated water level drops below a pre-defined threshold for some time, a water out alarm is raised.

The threshold is dependent on the flow rate and can be determined empirically. With water in the chamber, the system is allowed to reach steady state regarding flow rates within the operating range. Then, without water in the chamber, the system is tested with the same flow rates. The result is two values, a water in value and a water out value.

In some embodiments, the threshold is set half way between these two values. As the user selects different therapy modes, the threshold value can be adjusted according to the selected therapy mode's particular set point value.

Since the estimated water level is based on heater plate power, which may fluctuate due to pulsatile flow, controller stability, etc., in some embodiments, a timer is used to wait a set period of time with the estimated water level below the threshold value before activating the alarm. In some embodiment, this is set to 15 minutes for low flow rates and 10 minutes for higher flow rates. There is also a separate settling timer for preventing false triggers due to set point changes, flow rate changes, etc. In some embodiments, this is set to 20 minutes.

In some embodiments, once the humidification chamber 5 is filled with water following a water out condition alarm, the alarm will be deactivated when the estimated water level rises above the threshold.

Active Water Out Detection

According to the present disclosure, in certain circumstances, an active water out detection method of the water out condition is made in response to the passive water out detection method determining a water out condition. According to some embodiments, during the active water out detection method, the controller 8 takes control of the humidifier power input, adjusts the heater plate power input and observes the temperature response of the heater plate 12. This active water out detection method is implemented in certain circumstances to confirm the water out condition when the passive water out detection method returns a possible water out condition.

In some embodiments, the passive water out detection method may be used without the active test; however, this may sacrifice some accuracy at low flow rates. In alternative embodiments, the active test may be used without the passive test; however, this may be more intrusive to the delivery of therapy and the execution of other modules, such as the low temperature alarm.

In some embodiments, the active water out detection method may be used to confirm a water out condition since a passive water out detection method may falsely determine a water out condition under certain operational states. These states include the third and fourth operational states, as discussed above. The likelihood of the passive water out detection method returning a false positive increases for lower set points because the denominator of the estimated water level ratio, as described above, gets too close to zero. This occurs because the heater plate temperature is also lowered, causing the two denominator values to become closer in range. This occurs since both the heater plate temperature and the chamber outlet temperature are closer to ambient. Therefore, the heater plate does not have to work as hard to achieve the chamber outlet target temperature.

According to the present disclosure, after the passive water out detection method determines a water out condition, the controller 8 begins performing the active water out detection method when the system is in the third or fourth operational states.

Figure 3:
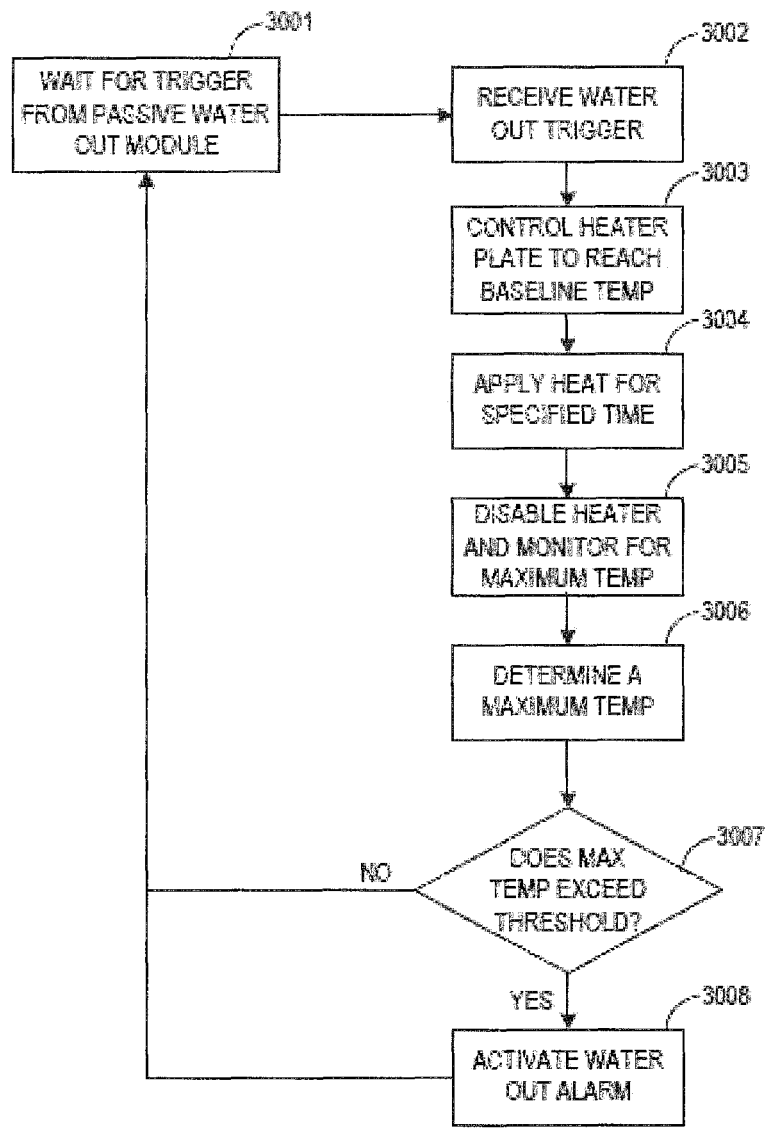
FIG. 3 is a flow diagram illustrating an active water out detection method for determining an absence of water in a humidifier chamber in accordance with the present disclosure.

During an active test, the controller 8 takes control of the heater plate feedback mode and duty cycle calculations in accordance with the routine described below. As illustrated in FIG. 3, the active water out detection method involves pulsing the heater plate 12 with a fixed power for a short duration and observing the rise of the heater plate 12 temperature. When the humidification chamber 5 is dry, the effective thermal mass of the heater plate is reduced and a higher peak heater plate temperature is expected. Upon completion of the active water out detection method, the controller 8 transitions to step 3001 and control of the heater plate feedback mode and duty cycle calculations is then returned to the normal heater plate control algorithm and PI controller.

As illustrated in FIG. 3, according to the routine, the controller 8 performs the following active water out detection method described below.

As shown in step 3001, the system waits for a trigger resulting from the passive water out detection method returning a water out condition while the system is under a third or fourth operational state. In this state, the heater plate control mode is normal and uses chamber outlet feedback. If the system receives a water out condition trigger, as shown in step 3002, the system is due for an active water out detection test and will transition to the next step.

At step 3003, the controller 8 controls the heater plate temperature to a baseline, so that the starting condition of the test is controlled. To achieve a baseline, the system switches off, reduces power supplied or provides constant power to the heater plate 12 at a low enough level to achieve the desired baseline level. The heater plate temperature must then remain within 0.1° C. for 15 seconds prior to the controller 8 transitioning to the next step.

At step 3004, the controller 8 adjusts the heater plate's duty cycle to apply 150 W to the heater plate 12 for 10 seconds. The controller 8 then transitions to the next step.

At step 3005, the controller 8 disables the heater plate power and monitors the temperature of the heater plate 12 for maximum heater plate temperature with a heater plate sensor. The temperature curve is monitored until a maximum temperature is reached.

The maximum heater plate temperature is determined by any suitable method at step 3006. A method of determining the maximum temperature is by taking a first derivative of the temperature signal and indicating the maximum temperature when the derivative is equal to 0. Alternatively, the system can wait until there is a reduction in temperature and utilizing the measurement immediately before the reduction as the maximum temperature. As soon as the maximum heater plate temperature is reached, the system transitions to the next step.

At step 3007, the system determines whether the maximum heater plate temperature exceeds a predetermined threshold. The threshold is set at halfway between the estimated heater plate temperature rise when the chamber is full and the estimated heater plate temperature rise when the chamber is dry. The mathematical formulas for the calculation of the threshold value are included below:

Heater Plate Temperature Threshold=0.5*Estimated Heater Plate Temperature Full+(1−0.5)*Estimate Heater Plate Temperature Dry Estimated Heater Plate Temperature Full=5.377− 0.052*Heater Plate Temperature Baseline− 0.017*Filtered Flow Rate Estimated Heater Plate Temperature Dry=6.970− 0.040*Heater Plate Temperature Baseline− 0.017*Filtered Flow Rate The threshold can be adjusted for ambient conditions and flow rate, among other parameters. In some alternative embodiments, the system may automatically adjust thresholds based on changes in other parameters. Alternatively, the system may have a preset number of stored thresholds for various environmental parameters.

If the maximum heater plate temperature or the measured temperature after 10 seconds does not exceed a threshold level, then the controller 8 determines that the water is not out. The controller 8 transitions to step 3001 and waits for the next request for an active water out detection test. In some embodiments, the controller 8 may do nothing prior to transitioning to step 3001. Alternatively, the controller 8 may message the user stating that there is enough water before returning to step 3001.

As soon as the maximum heater plate temperature or the measure temperature after 10 seconds exceeds the threshold level, the controller 8 activates the alarm at step 3008. The alarm can be a visual alarm, a message, an animation, or an audible alarm. After the alarm is activated, the controller 8 may transition to step 3001 and wait for the next request for an active water out detection test.

Figure 7:
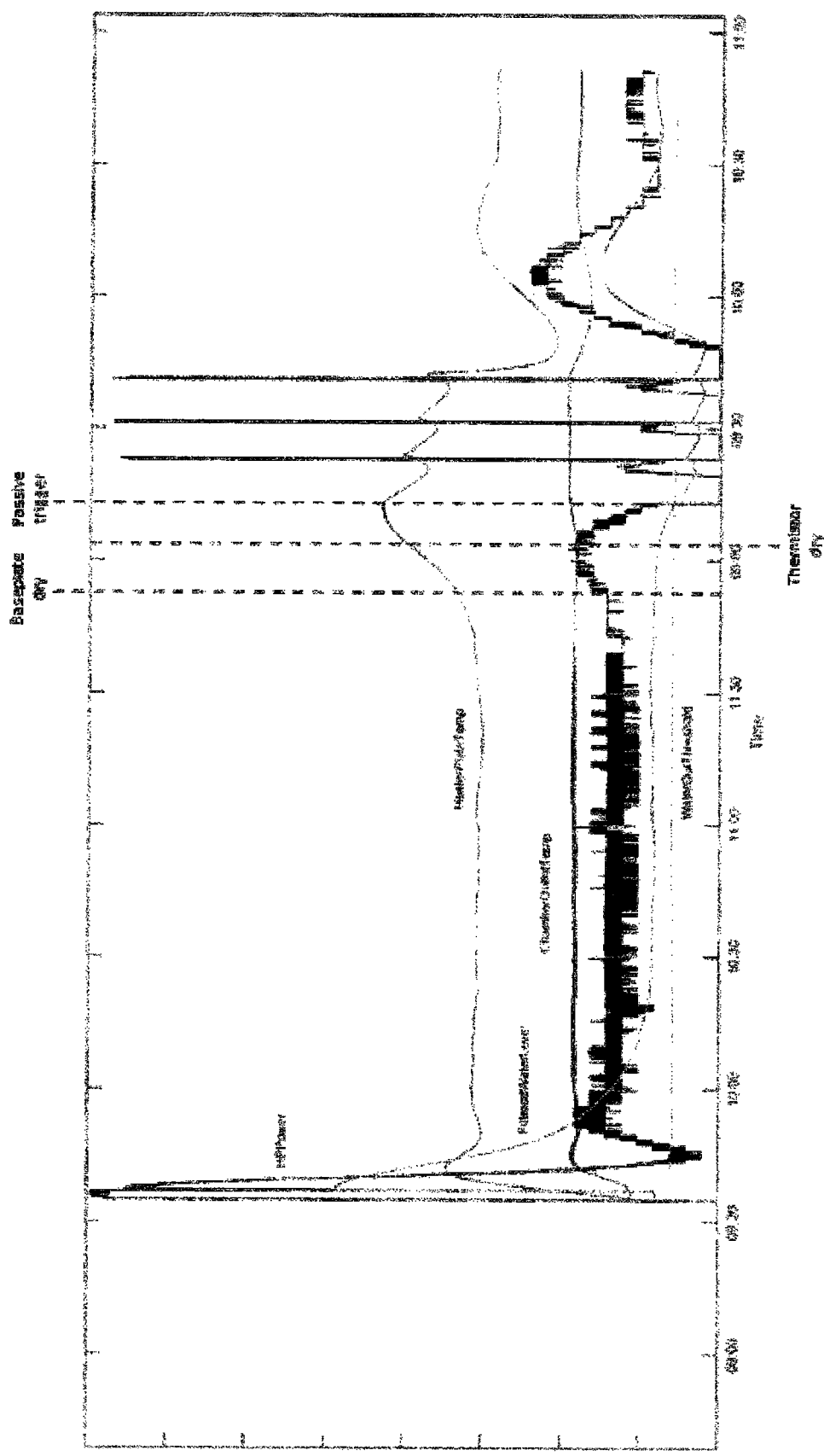
FIG. 7 is a plot against time of a function of heater plate power, heater plate temperature, filtered water level, and chamber outlet temperature, according to an experiment conducted to test a water out detection method using the present disclosure.

An example of this monitoring function is illustrated in FIG. 7. This graph shows data captured during a test of the routine selecting the appropriate water out detection method. Moving in time from left to right, the heater plate power (shown as HPPower) spikes at system start up and then settles to a steady state, as do the heater plate temperature, the chamber outlet temperature, and the filtered water level, previously referred to as the estimate water level.

A first phase is reached as the water in the humidification chamber 5 runs out. At this moment, the baseplate is dry but the chamber outlet temperature sensor is still wet from condensation. The temperature sensor returns lower values even though the gas temperature is not dropping. This occurs because the wet temperature sensor measuring dry gas introduces error. The heater plate power increases to compensate the decrease in the temperature values. As a result, the heater plate temperature rises as well, but faster than usual due to the absence of water on the baseplate. The filtered water level starts to drop because of this change in the ratio.

A second phase is reached after the temperature sensor is dried and the error is no longer present. The heater plate power decreases correspondingly, but the heater plate temperature continues to rise because the air above the baseplate does not absorb as much heat as water would have. This causes the filtered water level to drop even more steeply as the heater plate power and heater plate temperature continue to diverge.

A third phase is reached when the filtered water level drops below the water out threshold. In this example, the therapy mode is set to non-invasive or the flow rate is low to medium, which causes the active water out detection method to be initiated. Each of the spikes in heater plate power reflects an execution of the test (i.e., the state machine transitions to step 3004). After the third spike, the humidification chamber 5 is refilled with water, causing the heater plate temperature to drop drastically. This, in turn, causes the heater plate power increases to heat the added cold water.

System Therapy Modes

According to the present disclosure, the respiratory assistance system may be placed in one of several therapy modes. The selected therapy mode alters certain set point and threshold values during the controller's 8 determination of the appropriate water out detection method. In particular, the therapy mode may alter the specific gases flow rate of the system.

In some embodiments, the therapy modes may be selected from one of either an invasive mode, a non-invasive mode, or an Optiflow® mode. The Optiflow® mode is utilized when the application requires a high flow rate through an unsealed interface.

As described, each therapy mode has individualized set points. In some embodiments, the non-invasive mode may comprise set points of 31 degrees, 29 degrees and 27 degrees Celsius. The Optiflow® mode may comprise set points of 37 degree, 35 degree and 33 degrees Celsius. The invasive mode may comprise set points of 37 degrees Celsius.

In some embodiments, the system may comprise a user interface configured to permit a user to select the respective therapy mode.

Gases Flow Rates

According to the present disclosure, the respiratory assistance system may also be configured to provide a variety of gases flow rates. The selected flow rate alters the system's determination of the appropriate water out detection method. In particular, the flow rate may alter the particular system operational state of the system.

In some embodiments, the flow rate may be selected from one of either a no flow rate, a low flow rate, a medium flow rate, or a high flow rate. As described, each flow rate has an individualized classification range. In some embodiments, the no flow rate may comprise a rate between 0 L/min-3.5 L/min. The low flow rate may comprise a rate between 3 L/min-7 L/min. The medium low flow rate may comprise a rate between 5 L/min-15 L/min. The medium high flow rate may comprise a rate between 13 L/min-35 L/min. The high flow rate may comprise a rate greater than 30 L/min.

The ranges of each flow rate category can overlap with other categories. In order to move from one flow rate category to the next, the flow rate needs to exceed the upper limit of the category or drop below the lower limit of the category. For example, if the current flow rate is the low flow category, the flow rate will need to exceed 7 L/min in order to move into the medium low category. Similarly, in order to move back down to the low category once within the medium low category, the flow rate will need to drop below 5 L/min. The overlapping ranges can help to prevent constantly switching categories for flow rates that are fluctuating close to a threshold.

Design Considerations

Baseline Temperature

Since the heater plate temperature increase is dependent on the baseline temperature, the test range for the threshold design should include the minimum and maximum expected heater plate temperatures within the intended operating range. To minimize effects on passive alarms and therapy delivery, the baseline temperature should be close to the operating heater plate temperature. If there is an enthalpy concern, then the baseline temperature should be lower than the operating heater plate temperature, but this may increase test cycle time.

Flow Rate

The same analysis described under Baseline Temperature applies for flow rate, as well. The test range should include the expected operating range.

Open Loop Duty Cycle

An open loop duty cycle is applied, which gives a good rectangular pulse in power and is not affected by the controller 8. The duty cycle is based on the measured mains voltage from the PMIC, the measured heater plate resistance, and the desired power.

Power Applied

In some embodiments, 150 W is selected because the heater plate is able to deliver it even if the mains voltage is reduced by 10% (given the nominal heater plate power is 200 W). If the delivered power were higher, the heater plate may not be able to deliver the same power when connected to a lower mains voltage. If it were lower, the heater plate temperature rise may be reduced which could increase the possibility of false alarms.

Power Application Time

In some embodiments, 10 seconds is selected so the effect from timing jitter can be reduced while minimizing the possibility of generating excessive humidity. (Note: if the timer implementation changes and affects the duration of the pulse, then the threshold needs to be re-determined)

Detection Criteria

Maximum heater plate temperature is used as the detection metric because of consistency, good signal-to-noise ratio between dry and wet chambers, low computational complexity, and faster test cycle time.

Minimum Time in Step 3005

Due to the delay between the application of power and the heater plate temperature response, the controller 8 stays in step 3005 long enough to observe an increase in heater plate temperature before exiting when the temperature drops below the maximum.

Potential Interruption

Since the test takes a non-negligible amount of time to complete, it is possible that external events may affect the outcome. Possible events include: a water refill, a flow rate or pattern change, a therapy mode change, a set point change (due to user or humidity compensation), an inspiratory circuit or sensor cartridge disconnection, and a power on or off.

In the event of a water refill, the heater plate temperature will decrease. However, this is good as a lower temperature indicates water is present.

Interaction with Low Temperature Alarm

Since the active water out detection method interrupts normal heating, the heater plate and chamber outlet temperatures will be affected. The routine attempts to minimize this effect by setting the baseline temperature close to the current operating heater plate temperature. An active water out detection method is expected to be completed well within 10 minutes, thus the low temperature alarm (which takes between 10 and 60 minutes to trigger, depending on the therapy and set point) should not raise a false alarm.

Timeout and Return to Default State

If the system is unable to satisfy the conditions for a state transition, a timeout will occur and the state will return to step 3001. In an embodiment of the device, the timeout values may be as follows:

Step 3003 timeout=15 minutes
Step 3004 timeout=15 seconds
Step 3005 timeout=5 minutes Not Enough Energy Delivered Due to timing or lower than expected mains voltage, the system may not deliver the required power over time. Power measurements made by the PMIC will be recorded to assess the energy pulse delivered during the active testing phase. In some embodiments, if the power is under-delivered or over-delivered, the system will retry 3 times. If all retries fail, the system will disable the active water out detection method (because it affects the passive water out detection method) and fall back to the passive water out detection method.

Test Duration

Test duration is minimized to reduce the disruption to normal therapy by allowing an active water out detection method to start at various baseline heater plate temperatures.

Examples of respiratory humidification systems and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate the principles and details regarding divisions of modules or systems have been provided for ease of description rather than attempting to delineate separate physical embodiments. The examples and figures are intended to illustrate and not to limit the scope of the inventions described herein. For example, the principles herein may be applied to a respiratory humidifier as well as other types of humidification systems, including surgical humidifiers. The principles herein may be applied in respiratory applications as well as in other scenarios for determining whether water is available within a respiratory system.

As used herein, the term "processor" refers broadly to any suitable device, logical block, module, circuit, or combination of elements for executing instructions. For example, the controller 8 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor or a microcontroller. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module 504 can be a software-implemented function block which does not utilize any additional and/or specialized hardware elements. Controller 8 can be implemented as a combination of computing devices, e.g., a combination of a DSP and a microprocessor, a combination of a microcontroller and a microprocessor, a plurality of microprocessors, one or more microprocessors in conjunction with a DSP core, or any other such configuration.

Data storage can refer to electronic circuitry that allows data to be stored and retrieved by a processor. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller 8. Other types of data storage include bubble memory and core memory. Data storage can be physical hardware configured to store data in a non-transitory medium.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within ±10%, within ±5%, or within ±1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A respiratory assistance system for humidifying a flow of gases, the respiratory assistance system comprising:
   a heater configured to provide heat to a quantity of water held in a humidification chamber;
   a flow sensor;
   a temperature sensor configured to sense a temperature of the gases proximal to an outlet of the humidification chamber; and
   a controller in electronic communication with the heater, the flow sensor and the temperature sensor,
   wherein the controller is configured to determine at least one operational state from a plurality of predetermined operational states based on at least one of a temperature of the heater, a temperature of the gases proximal to the outlet of the humidification chamber, or a therapy mode and a flow rate, and
   wherein the controller is further configured to select at least one independently selectable water out detection method from a plurality of water out detection methods based on the determined operational state, wherein the at least one water out detection method is selected from one or more predetermined water out detection methods associated with the determined operational state.

2. The respiratory assistance system of claim 1, wherein the operational state is dependent on the flow rate in relation to a flow rate threshold.

3. The respiratory assistance system of claim 1, wherein the flow sensor detects the flow rate, the flow sensor proximal an inlet or the outlet of the humidification chamber.

4. The respiratory assistance system of claim 1 further comprising a user interface configured to permit a person to select the therapy mode from a predetermined list of therapy modes,
   wherein the predetermined list comprises an invasive mode, a non-invasive mode, and a high flow, unsealed mode, and
   wherein the high flow, unsealed mode comprises a high flow rate through unsealed interface.

5. The respiratory assistance system of claim 4, wherein the therapy mode comprises a plurality of set points.

6. The respiratory assistance system of claim 5, the non-invasive mode comprising set point of 31 degrees, 29 degrees, and 27 degrees Celsius; and/or the high flow, unsealed mode comprising set points of 37 degrees, 35 degrees, and 33 degrees Celsius; and/or the invasive mode comprising a set point of 37 degrees Celsius.

7. The respiratory assistance system of claim 1, the predetermined plurality of operational states comprise:
   a startup operational state relating to the temperature of the heater below a defined temperature threshold and/or the temperature for the outlet of the humidification chamber below a defined temperature threshold,
   a first operational state relating to a no flow state,
   a second operational state relating to a therapy mode having a high set point and a medium high or high flow rate,
   a third operational state relating to a therapy mode having the high set point and a medium low or low flow rate,
   a fourth operational state relating to a therapy mode having a low set point.

8. The respiratory assistance system of claim 7, wherein:
   the high set point has a temperature above 31 degrees Celsius and the low set point has a temperature between and including 25 degrees and 31 degrees Celsius; and/or
   the defined temperature threshold of the heater is greater than or equal 30 degrees Celsius and/or is 40 degrees Celsius; and/or
   the defined temperature threshold for the outlet of the humidification chamber is greater than or equal to 30 degrees Celsius and/or is 37 degrees Celsius; and/or
   the no flow state has a flow rate between 0 l/min and 3.5 l/min, the low flow rate has a flow rate between 3 l/min and 7 l/min, the medium low flow rate has a flow rate between 5 l/min and 15 l/min, the medium high flow rate has a flow rate between 13 l/min and 35 l/min, and the high flow rate has a flow rate greater than 30l/min.

9. The respiratory assistance system of claim 7, wherein the controller is configured to perform at least one of the following:
   disable the water out detection method when in the first operational state,
   select a passive water out detection method when in the second operational state, or
   select the passive water out detection method when in the third or fourth operational state.

10. The respiratory assistance system of claim 1, the at least one independently selectable water out detection method from a plurality of water out detection methods comprising a passive water out detection method, an active water out detection method, and the passive water out detection method in conjunction with the active water out detection method.

11. The respiratory assistance system of claim 10, the passive water out detection method comprising:
   calculating an estimated water level;
   comparing the estimated water level to a threshold; and
   determining a water out condition when the estimated water level is less than the threshold.

12. The respiratory assistance system of claim 11, the estimated water level comprising a ratio of an amount of power supplied to the heater divided by the difference between a temperature of the heater minus a temperature of humidified gases proximal to the outlet.

13. The respiratory assistance system of claim 12, wherein the power supplied to the heater is determined by a heater plate power sensor, wherein the heater plate power sensor comprises a PMIC.

14. The respiratory assistance system of claim 10, the active water out detection method comprising:
   controlling the temperature of the heater to a baseline;
   supplying an amount of power to the heater until a target is achieved;
   monitoring the heater temperature until a maximum is reached; comparing the maximum heater temperature to a threshold; and determining a positive test result when the maximum heater temperature is greater than the threshold.

15. The respiratory assistance system of claim 10, the passive water out detection method in conjunction with the active water out detection method comprising:
   determining a water out condition through the passive water out detection method; and
   confirming the water out condition through the active water out detect method if the passive water out detection method provided a positive outcome.

16. The respiratory assistance system of claim 1, the therapy mode relating to a mode value received by the controller and/or the therapy mode selected by a user.

17. The respiratory assistance system of claim 1 further comprising the humidification chamber, wherein the humidification chamber is adapted to hold the quantity of water, the humidification chamber having an inlet and the outlet to allow gases to pass through the humidification chamber, and the flow sensor is positioned on the humidification chamber.

18. The respiratory assistance system of claim 9, wherein the controller is configured to perform at least one of the following:
   select an active water out detection method when in the third or fourth operational state if the passive water out detection method returns a water out condition, or
   select a time-based active water out detection method when in the fourth operational state.

* * * * *